US00PP28548P2

(12) United States Plant Patent
Sills et al.

(10) Patent No.: US PP28,548 P2
(45) Date of Patent: Oct. 24, 2017

(54) BLACKBERRY PLANT NAMED 'DRISBLACKSIXTEEN'

(50) Latin Name: ***Rubus* L. subgenus *Rubus***
Varietal Denomination: DrisBlackSixteen

(71) Applicant: Driscoll's, Inc., Watsonville, CA (US)

(72) Inventors: Gavin R. Sills, Gilroy, CA (US); Jorge Rodriguez Alcazar, Texcoco (MX); Andrea M. Pabon, Gilroy, CA (US); Mark F. Crusha, Capitola, CA (US); Missael Bonifacio Romero Escobedo, Jalisco (MX)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 14/999,063

(22) Filed: Mar. 25, 2016

(51) Int. Cl.
*A01H 5/08* (2006.01)

(52) U.S. Cl.
USPC ..... Plt./203

(58) Field of Classification Search
USPC ..... Plt./203
CPC ..... A01H 5/0887
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear |
| PP13,758 | P3 | 5/2003 | Fear |
| PP13,759 | P3 | 5/2003 | Fear |
| PP14,682 | P3 | 4/2004 | Fear |
| PP14,765 | P2 | 5/2004 | Fear et al. |
| PP14,780 | P2 | 5/2004 | Fear et al. |
| PP15,058 | P2 | 8/2004 | Fear et al. |
| PP17,162 | P3 | 10/2006 | Clark et al. |
| PP17,983 | P2 | 9/2007 | Cabrera Avalos |
| PP22,002 | P2 | 7/2011 | Sills et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Sills et al. |
| PP24,701 | P3 | 7/2014 | Sills et al. |
| PP24,878 | P2 | 9/2014 | Sills et al. |
| PP25,502 | P3 | 5/2015 | Sills et al. |
| PP26,501 | P3 | 3/2016 | Sills et al. |
| PP26,611 | P3 | 4/2016 | Sills et al. |
| PP26,774 | P3 | 5/2016 | Sills et al. |
| PP27,129 | P2 | 9/2016 | Sills et al. |
| PP27,130 | P2 | 9/2016 | Sills et al. |
| PP27,146 | P2 | 9/2016 | Sills et al. |
| 2016/0183424 | P1 | 6/2016 | Sills et al. |
| 2016/0183425 | P1 | 6/2016 | Sills et al. |
| 2016/0249505 | P1 | 8/2016 | Sills et al. |

OTHER PUBLICATIONS

Voss, Donald H., "The Royal Horticultural Society Colour Chart 2001", Journal American Rhododendron Society, vol. 56, No. 1, 2001, 3 pages.
Williams et al., "DNA polymorphisms amplified by arbitrary primers are useful as genetic markers", Nucleic Acids Research, vol. 18, No. 22, 1990, pp. 6531-6535.

*Primary Examiner* — Kent L Bell
(74) *Attorney, Agent, or Firm* — Morrison & Foerster LLP

(57) ABSTRACT

This invention relates to a new and distinct variety of blackberry plant named 'DrisBlackSixteen', particularly characterized by having high vigor, large-sized, dark greyish-purple berries and self-fruitful plants, is disclosed.

2 Drawing Sheets

Genus and species: *Rubus* L. subgenus *Rubus*.
Variety denomination: 'DrisBlackSixteen'.

BACKGROUND OF THE NEW PLANT

The present invention relates to a new and distinct blackberry cultivar designated 'DrisBlackSixteen' and botanically known as *Rubus* L. subgenus *Rubus*. This new blackberry variety was discovered in Ventura County, Calif. in April 2009 and originated from a cross between the proprietary female parent blackberry plant 'DrisBlackFive' (U.S. Plant Pat. No. 24,701) and the proprietary male parent blackberry plant 'BL481.2' (unpatented). The original seedling of the new cultivar was first asexually propagated by tissue culture and root cuttings at a nursery in Santa Cruz County, Calif. in 2010. 'DrisBlackSixteen' was subsequently asexually propagated by tissue culture and root cuttings and underwent further testing at a nursery in Michoacan, Mexico, from 2011 to 2015. The present invention has been found to be stable and reproduce true to type through successive asexual propagations.

SUMMARY OF THE INVENTION

The following are the most outstanding and distinguishing characteristics of this new cultivar when grown under normal horticultural practices in Michoacan, Mexico.

1. High vigor;
2. Large sized, dark greyish-purple berries; and
3. Self-fruitful plants.

DESCRIPTION OF THE PHOTOGRAPHS

This new blackberry plant is illustrated by the accompanying photographs which show the plant's canes, flowers, fruit, and leaves. The colors shown are as true as can be reasonably obtained by conventional photographic procedures. The photographs are of plants that are 2 years old.

Figure 1:
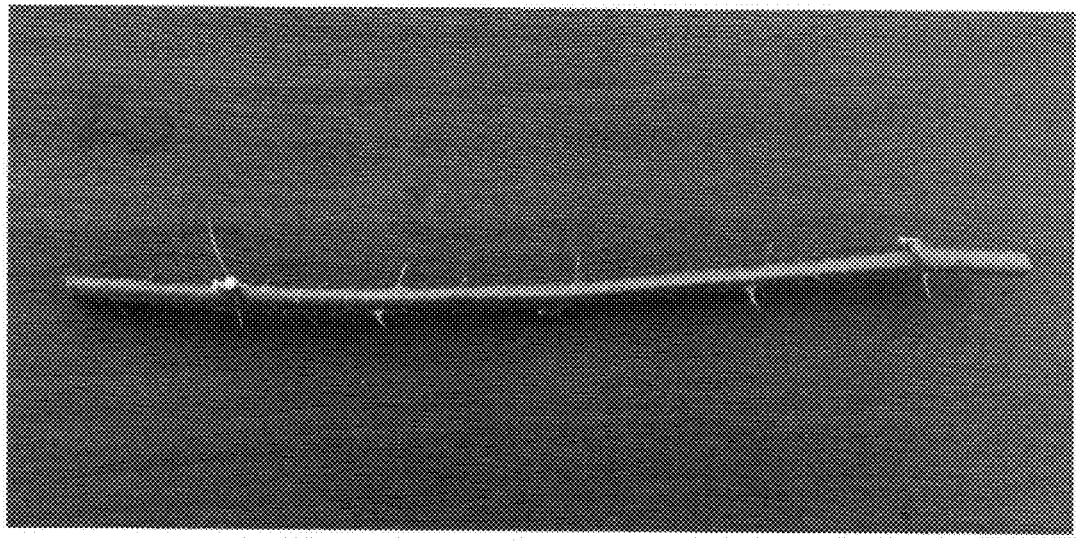
Figure 2:
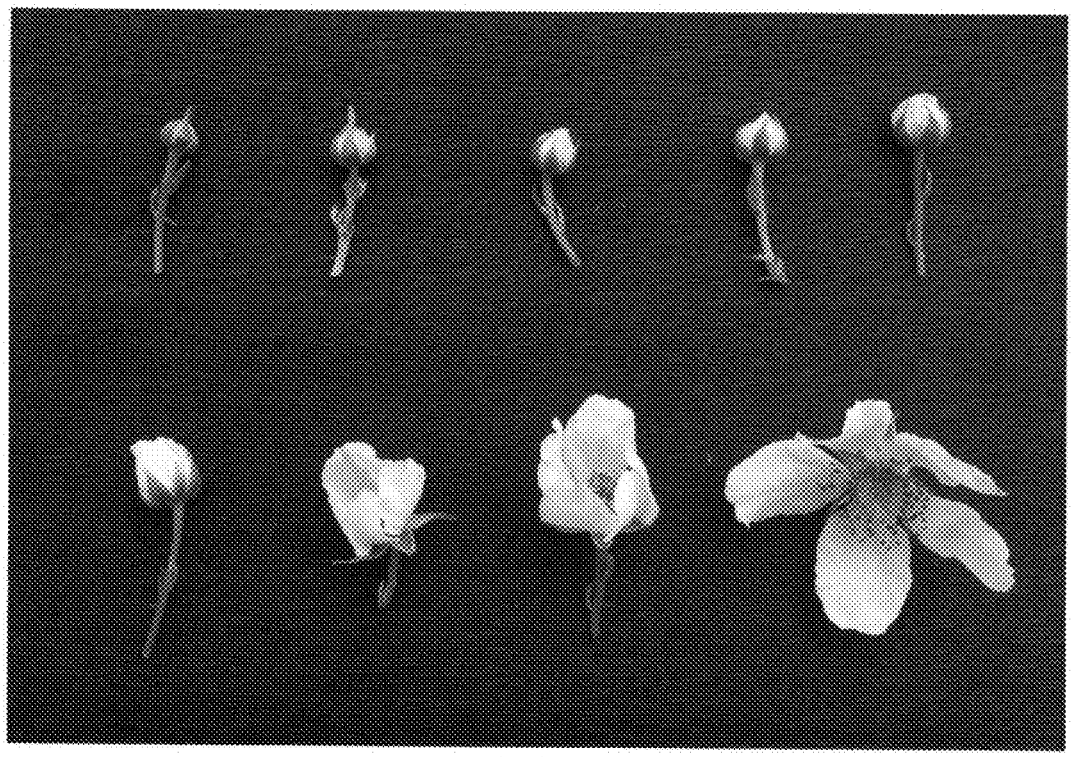
Figure 3:
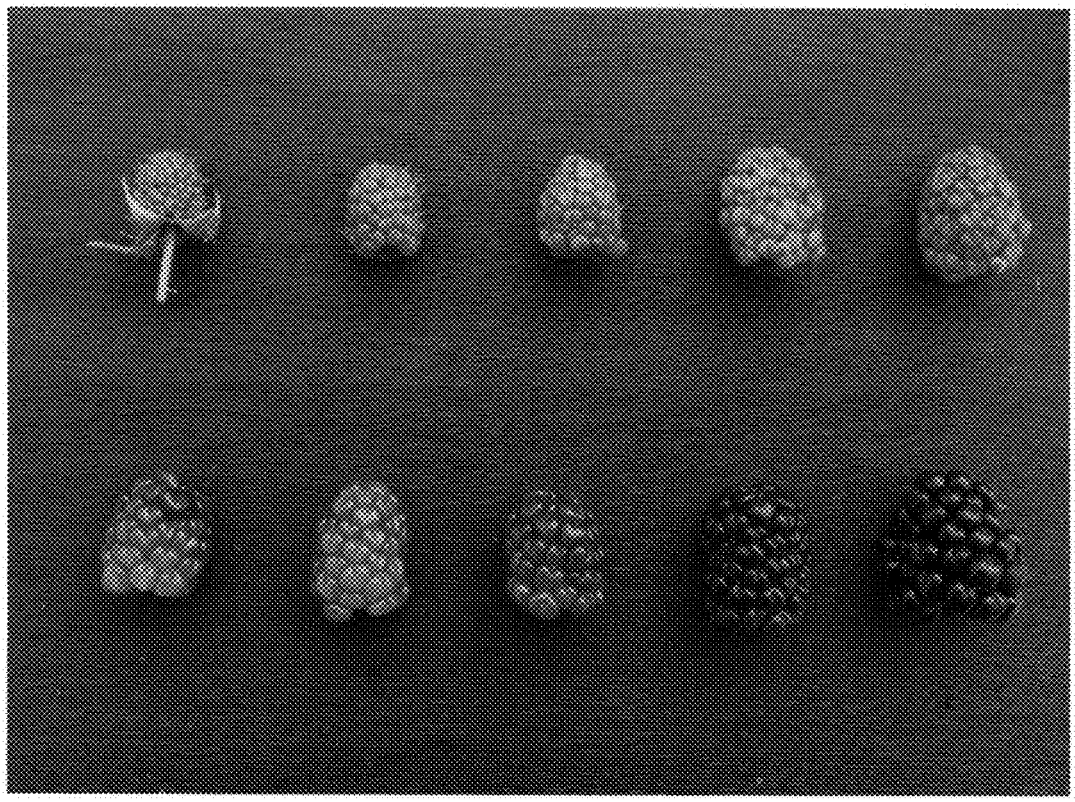

FIG. 1 shows a section of a young cane with spines.
FIG. 2 shows the flowers at various stages.
FIG. 3 shows the fruit at various stages.

DESCRIPTION OF THE NEW VARIETY

The following descriptions of 'DrisBlackSixteen' are based on observations made in Michoacan, Mexico on 2-year old plants. This description is in accordance with UPOV terminology. Color designations, color descriptions, and other phenotypical descriptions may deviate from the stated values and descriptions depending upon variation in environmental, seasonal, climatic and cultural conditions. 'DrisBlackSixteen' has not been observed under all possible environmental conditions. Color terminology follows The Royal Horticultural Society Colour Chart, London (R.H.S.) (2015 edition). Descriptive terminology is from the *Plant Identification Terminology, An Illustrated Glossary* 2$^{nd}$ edition, by James G. Harris and Melinda Woolf Harris, unless where otherwise defined.

DETAILED BOTANICAL DESCRIPTION

Classification:

*Family*.—Rosaceae.

*Botanical*.—*Rubus* L. subgenus *Rubus*.

*Common name*.—Blackberry.

*Variety name*.—'DrisBlackSixteen'.

Parentage:

*Female parent*.—Proprietary blackberry plant named 'DrisBlackFive' (U.S. Plant Pat. No. 24,701).

*Male parent*.—Proprietary blackberry plant named 'BL481.2' (unpatented).

Plant:

*Vigor*.—High.

*Growth habit*.—Semi-upright to spreading.

*Productivity*.—Productivity from plants that were two-years old ranged from 17,500 pounds/acre to 22,500 pounds/acre per season.

*Propagation*.—Tissue culture and root cuttings.

*Self-fruitfulness*.—Self-fruitful.

*Time of leaf bud burst*.—June to July.

Canes:

*Fruiting lateral length* (4$^{th}$ *lateral from tip*).—Long; 44.2 cm.

*Number of fruit per lateral*.—21.

*Fruiting on current year's cane*.—Present.

*Cane internodal distance*.—5.7 cm.

*Number of new canes during flowering*.—3 to 4.

*New cane strength* (*observed full-grown shoot after picking*).—Medium.

*Glaucosity* (*observed on full-grown shoot after picking*).—Weak.

*Young shoots*.—Quantity: 8 to 10. Time of emergence from soil: May. Anthocyanin coloration (during rapid growth): Weak; RHS 178A (Greyish-red). Intensity of green color: Medium; RHS 144A (Strong yellow-green). Number of glandular hairs: Medium.

*Dormant cane*.—Length: 1.5 meters to 2.5 meters. Diameter (in central third): 15.25 mm to 18.38 mm. Color: RHS 138B (Moderate yellow-green). Cross section (from mid cane observed at end of first growing season): Rounded. Number of branches: 4 to 6. Distribution of branches: Only on upper third. Anthocyanin coloration: Medium; RHS178B (Dark reddish-orange). Spines: Number of spines: 405 per 1.25-meter-long cane. Size: Medium. Color: RHS 181A (Moderate red). Density (on central third of cane): 5 to 7 spines/cm$^2$. Texture: Medium. Attitude of apex in relation to cane: Outwards.

Leaves:

*Type*.—Palmate.

*Predominant number of leaflets*.—Five.

*Overlapping or relative position of lateral leaflets*.—Overlapping.

*Color*.—Upper surface: Dark; RHS 147A (Moderate olive-green). Lower surface: Light; RHS 146B (Moderate yellow-green).

*Glossiness of upper side*.—Medium.

*Cross section profile*.—Convex (margins rolled backwards).

*Leaflets*.—Shape: Ovate. Margin: Doubly serrate. Type of incision margin: Bi-serrate. Apex: Complex. Base: Obtuse. Rachis length between terminal leaflet and adjacent lateral leaflet: 45.0 mm. Rachis diameter: 1.98 mm to 2.12 mm.

*Lateral leaflet* (*basal pair*).—Length: 73.1 mm. Width: 56.7 mm. Length/width ratio: 1.3.

*Terminal leaflet*.—Length: Long; 85.1 mm. Width: Broad; 69.4 mm. Length/width ratio: 1.2. Lobing: Absent. Undulation of margin (rippling of margin): Medium. Blistering between veins (rugosity): Medium. Shape: Ovate. Tip: Truncate. Base: Obtuse. Margin: Doubly serrate. Cross-section: V-shaped.

*Petiole*.—Length: 21.8 mm. Diameter: 1.5 mm. Pigmentation: Upper surface: Medium; RHS 144A (Strong yellow-green). Lower surface: Light; RHS 173A (Dark reddish-orange).

*Stipule*.—Size: Large. Orientation: Reflexed. Number of stipules: 2 to 3. Shape: Linear type (long and slightly broader leaves). Length: 8.17 mm to 12.29 mm. Width: 0.78 mm to 0.91 mm. Color: Upper surface: RHS 138A. Lower surface: RHS 140B.

Inflorescence:

*Flower diameter*.—Medium; 40.80 mm.

*Flower number* (*at* 3$^{rd}$ *node from tip of lateral*).—5.

*Petal*.—Length: 20.62 mm Width: 14.17 mm. Length/width ratio: 1.5. Color: RHS 155C (Greenish-white).

*Pedicel*.—Length: 46.39 mm. Diameter: 1.05 mm. Color: RHS 144C.

*Time of beginning of flowering on previous year's cane*.—February to March.

Fruit:

*Size*.—Large.

*Shape*.—Long conical.

*Length*.—Long; 30.60 mm.

*Width*.—Medium; 23.40 mm.

*Ratio of length to width*.—Medium; 1.3.

*Weight* (*g/fruit*).—11.6 g.

*Soluble solids* (%) (*in brix*).—12.10.

*Titratable acidity*: (% *as citric acid*).—0.96.

*Seed weight* (*g/seed*).—0.005.

*Number of drupelets/fruit*.—Medium; 94.1.

*Color*.—Immature: RHS 146B (Moderate yellow-green). Maturing: RHS 181A (Moderate red). Mature: RHS 202A (Dark greyish-purple).

*Firmness*.—Firm.

*Glossiness*.—Strong.

*Shape in longitudinal section*.—Long conical.

*Time of ripening on previous year's cane*.—April to May.

*Harvest interval*.—Early January to late May.

*Yield*.—Yield from plants that were two-years old ranged from 17,500 pounds/acre to 22,500 pounds/acre per season.

Disease and stress resistance:

*Powdery mildew*.—Moderately susceptible.

*Fusarium oxysporum*.—Susceptible.

*Drought*.—Moderately resistant.

*High temperatures*.—Moderately resistant.

*Water logging*.—Moderately resistant.

COMPARISON WITH PARENTAL AND COMMERCIAL VARIETIES

'DrisBlackSixteen' differs from the proprietary female parent 'DrisBlackFive' (U.S. Plant Pat. No. 24,701) in that the fruit of 'DrisBlackSixteen' is firm with strong glossiness, whereas the fruit of 'DrisBlackFive' is very firm with medium glossiness. Additionally, the leaves of 'DrisBlackSixteen' are palmate shaped with medium glossiness, while the leaves of 'DrisBlackFive' are odd-pinnate shaped with weak glossiness.

'DrisBlackSixteen' differs from the proprietary male parent 'BL481.2' (unpatented) in that 'DrisBlackSixteen' has much larger fruit than 'BL481.2'. Additionally, 'DrisBlackSixteen' has spines, whereas 'BL481.2' is spineless.

'DrisBlackSixteen' differs from the commercial variety 'DrisBlackFour' (U.S. Plant Pat. No. 24,609) in that the leaves of 'DrisBlackSixteen' are medium glossy and palmate shaped with predominately 5 leaflets, whereas the leaves of 'DrisBlackFour' are very weakly glossy and odd-pinnate shaped, with predominately 3 leaflets. Additionally, plants of 'DrisBlackSixteen' have a semi-upright to spreading growth habit and high vigor, whereas plants of 'DrisBlackFour' have an upright growth habit and low vigor.

We claim:

1. A new and distinct variety of blackberry plant named 'DrisBlackSixteen', substantially as illustrated and described herein.

* * * * *